United States Patent [19]

Gonser et al.

[11] Patent Number: 5,003,434
[45] Date of Patent: Mar. 26, 1991

[54] MINIATURE HAND-HELD SPOT SOURCE OF ILLUMINATION

[75] Inventors: Donald I. Gonser; Douglas M. Reinhart, both of Lancaster, Pa.

[73] Assignee: Den-Tal-Ez, Inc., Valley Forge, Pa.

[21] Appl. No.: 554,180

[22] Filed: Jul. 13, 1990

Related U.S. Application Data

[63] Continuation of Ser. No. 252,041, Sep. 30, 1988, abandoned.

[51] Int. Cl.⁵ .............................................. B25K 25/18
[52] U.S. Cl. ...................................... 362/32; 362/119; 362/293; 362/804
[58] Field of Search ............... 362/109, 119, 120, 804, 362/32, 293; 128/303.1, 385, 396, 397, 398

[56] References Cited

U.S. PATENT DOCUMENTS

| | | | |
|---|---|---|---|
| 1,795,691 | 3/1931 | Wilson | 362/804 |
| 2,107,791 | 2/1938 | Henning | 362/804 |
| 2,428,975 | 10/1947 | Lamb | 362/32 |
| 2,885,537 | 5/1959 | Wood, Jr. | 362/119 |
| 3,704,928 | 12/1972 | Coombs et al. | 362/804 |
| 4,082,946 | 4/1978 | Heine et al. | 362/109 |
| 4,171,572 | 10/1979 | Nash | 362/32 |
| 4,330,274 | 5/1982 | Friedman et al. | 362/804 |
| 4,385,344 | 5/1983 | Gonser | 362/804 |
| 4,516,195 | 5/1985 | Gonser | 362/281 |
| 4,608,622 | 8/1986 | Gonser | 362/32 |
| 4,779,173 | 10/1988 | Carr et al. | 362/109 |

Primary Examiner—Ira S. Lazarus
Assistant Examiner—Richard R. Cole
Attorney, Agent, or Firm—Howson and Howson

[57] ABSTRACT

A miniature hand-held spot source of illumination particularly suited for use by health professionals to view and operate upon a patient's anatomy. The spot-source includes a handle with a tool mounted at its proximal end and a source for projecting light into the vicinity of the tool. The spot source is color corrected to enhance viewability under variety of ambient lighting conditions.

23 Claims, 5 Drawing Sheets

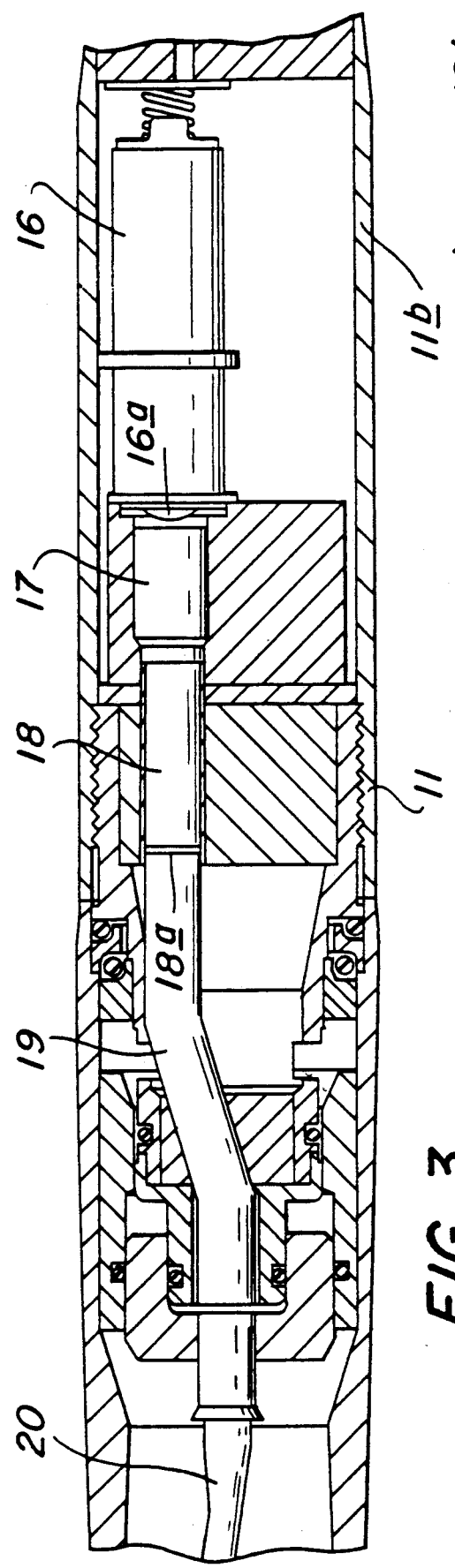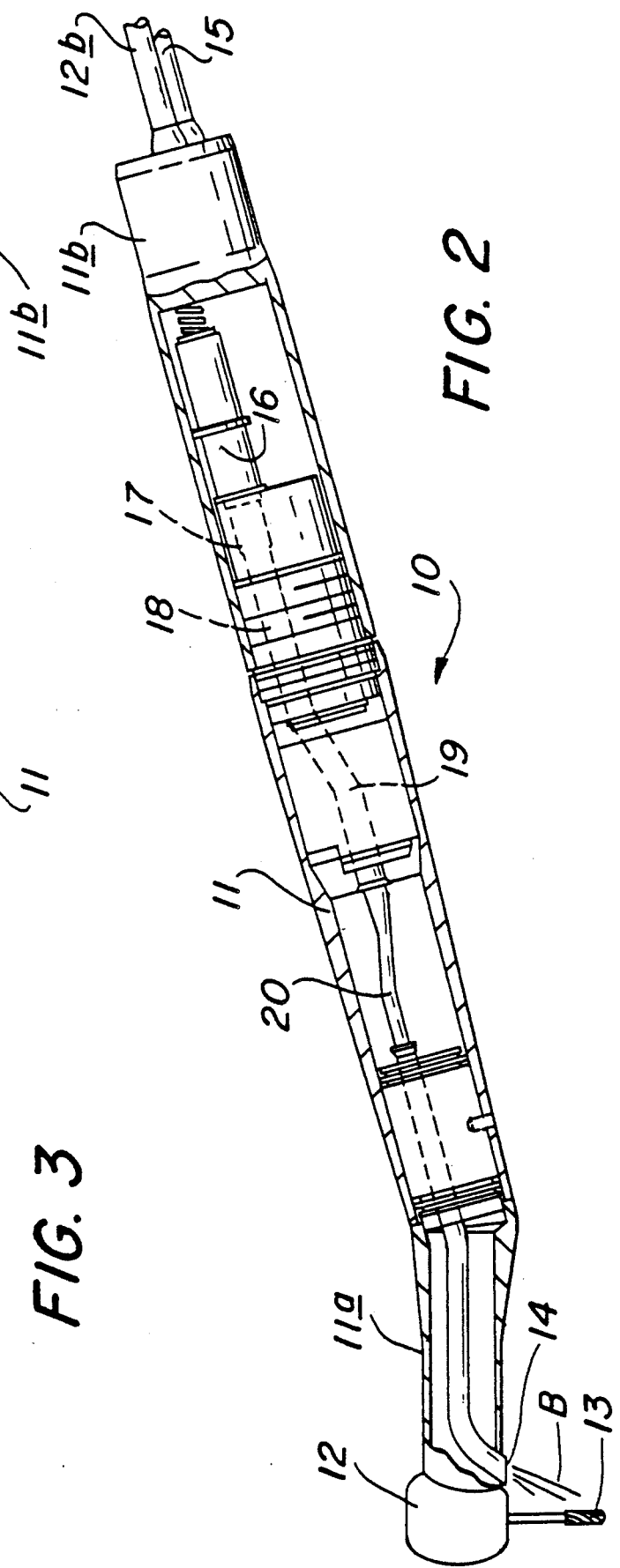

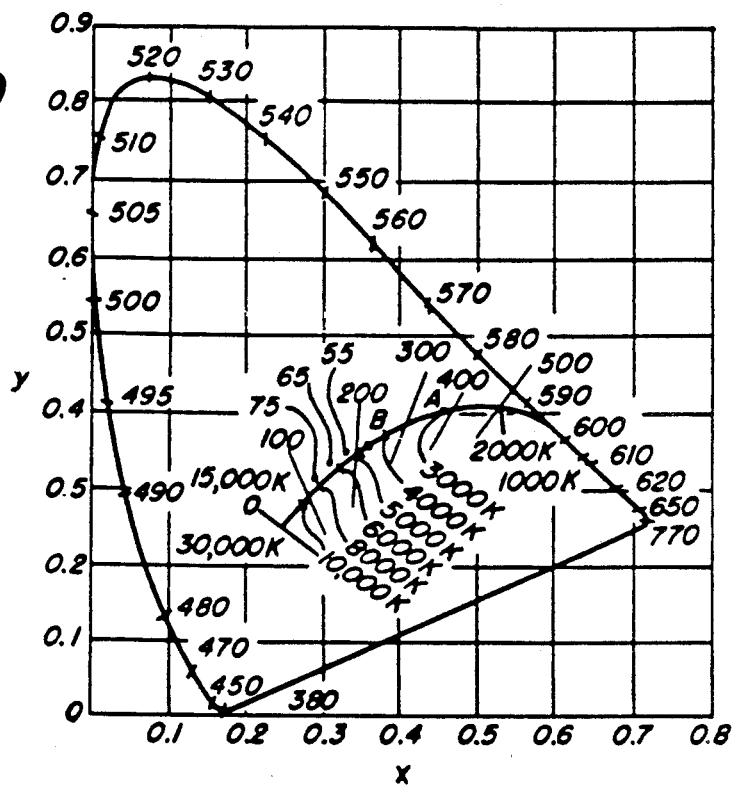
BLACK BODY CORRELATED COLOR TEMPERATURE DIAGRAM
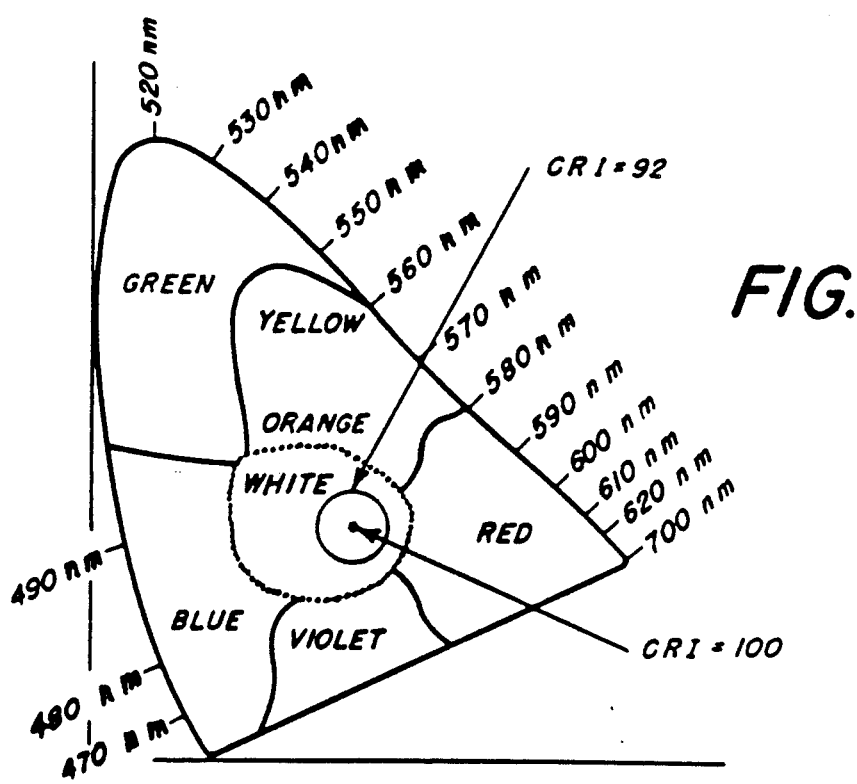
CHROMATICITY DIAGRAM (COLOR RENDERING INDEX)

MINIATURE HAND-HELD SPOT SOURCE OF ILLUMINATION

This is a continuation of co-pending application Ser. No. 07/252,041 filed on Sept. 30, 1988 now abandoned.

BACKGROUND OF THE INVENTION

The present invention relates to miniature hand-held spot sources of illumination, and more particularly, the present invention relates to such types of illumination as are useful by health professionals to observe and operate on patients.

The modern dental operatory may be provided with as many as four different sources of illumination. These may include a window transmitting light from outdoors, an overhead generalized source of illumination, a directable source of illumination, and a hand-held spot source of illumination which may, and generally is combined with a dental handpiece mounting a drill or burr. The directable source of illumination is provided for the purpose of generally illuminating the oral cavity, as may be desired. An example of a directable light source is disclosed in U.S. Pat. No. 4,608,622 issued to Gonser on Aug. 26, 1986.

Miniature hand-held spot sources of illumination are generally incorporated in a handle of the hand-held dental instrument. One or more light beams are projected laterally of the handle from the proximal end portion thereof onto the drill or burr. Light from a lamp in the handle is transmitted to the light beam projectors via an optical light path of conventional construction. The air supply for the drill or burr operating turbine is routed through the handle alongside the optical path.

In approximately 90% of the dental operatories in the U. S., the directable source of illumination is provided by a tungsten halogen lamp which produces a light having a yellow-hue. This quality of light is not as desirable as either sunlight or light which has been color corrected such as in the manner disclosed in the aforementioned patent. A major reason for this is that yellow-red light blurs the distinctions between various internal layers of a tooth, such as between the enamel and dentin. In addition, in the diagnosis of gum diseases, variations in color of tissue can be important, and such variations are less distinct under a source of illumination having a yellowish hue.

To compensate for what is perceived as a lower level of illumination, some health professionals often resort to increasing the intensity of the illumination to enable them to observe the anatomical distinctions noted above. This approach, however, is not in the long term best interest of the health professional because it may lead to eye damage. The reasons for this may best be explained in the context of the physiology of the eye.

Structurally, the eye comprises a cornea, a lens and a chamber which is filled with a gelatinous, vitreous humor behind which lies the retina. The retina is composed of nerve fibers known as rods and cones. The cones are responsive to colors, but they are relatively insensitive to low intensities of light so that color cannot be distinguished readily at such low intensities, i.e. twilight vision. The rods, however, are more sensitive to light because they contain a light-sensitive substance, but they cannot transmit color sensation.

A network of fine fibers connected to the retina transmit sensory impression through the optic nerve to the brain. Perception of color by the brain is not instantaneous. For example, blue sensations of light are perceived more quickly, and green sensations less quickly.

In the eye, the highest visual acuity occurs in one small central area in the retina known as the fovea centralis. The fovea is the center of a larger, specialized region known as the macula lutea (yellow spot). There is a depression in the retina known as the fovea depression in which many of the retinal layers are reduced in thickness. It is termed the foveal pit. The foveal pit contains the highest concentration of cone receptors which are responsible, not only for color vision, but also for vision of increased acuity.

The cones are packed tightly in the fovea. For instance, in the 100 micrometer diameter of central fovea, there are approximately 7,000 cones. In contrast, there are approximately 100,000 cones in the entire rod-free region, and there are over 4 million cones in the macula. In the peripheral portions of the retina outside the macula, the receptors include mostly rods. In the entire retina, there are approximately 7 million cones and 125 million rods which feed into approximately one million nerve fibers contained in the optic nerve.

There are psychophysical and psychological aspects involved in color perception. For instance, there are three types of cones that are sensitive to the three additive primary colors: red, blue and green which compose so-called white light. Light energy is converted into chemical energy through the mechanism of the visual pigments. When the eye is focused on a colored object, the visual pigments are depleted, and if they are depleted faster than they can be regenerated, color discrimination is lost. It is important, therefore, for good long-term eye health that colors be viewed under a perfectly balanced light source which activates all of the specialized cones and minimizes the color pigment depletion problem. This enables visual acuity and color discrimination to be maintained over a longer period of time.

It is known that sunlight contains a full spectrum of visible light of various wavelengths, including the primary additive colors red, blue and green. So-called white light artificial illumination, to be comparable to sunlight, should also contain a proper balance of light waves.

Systems have been devised for comparing the quality of light provided by artificial sources of illumination. Such a system includes reference to the term correlated color temperature (CCT). Correlated color temperature is the color temperature of a source of illumination which is equal to the temperature of a black body radiator heated to the temperature (in degrees Kelvin) necessary to produce that color. During heating, the black body undergoes a series of progressive color changes. For instance, initially, it glows red, then glows orange, yellow, white and finally blue respectively. Since an artificial light source does not actually generate the same thermal temperature as those corresponding to a black body possessing a particular color, the term correlated color temperature has been developed. For example, a candle glows at a correlated color temperature of 2,000 degrees Kelvin; a tungsten-halogen lamp glows at a correlated color temperature of about 3,200 degrees Kelvin; and a slightly overcast sky has a correlated color temperature in a range of about 5,500 to about 6,000 degrees Kelvin.

A properly balanced white light is characterized by the absence of hues. A system has been developed for quantifying the quality of light. This system includes a so-called color rendering index (CRI) and may be found in an algebraically derived chromaticity diagram. There is a point on the diagram representing a perfect balance of the various components of light, and this is referred to as an equal energy point. It is given a color rendering index of 100. Light with various hues, i.e. a red hue, a blue hue, etc. are charted at other locations on the chromaticity diagram. Hued light has a color rendering index of less than 100, depending on its distance from that point on the diagram. It has been determined that the highest efficiency of eye response in the dental operatory for the examination of anatomical structures of teeth and gingivas occurs when the color rendering index of the light used for examination purposes is 90 or greater.

While the quality of light required for anatomical examination purposes as described above is important, the quantity of light is also important. The dental operatory, for example, should have ambient lighting of at least about 150 footcandles (fc.). The source of illumination for the oral cavity, i.e. the directable source of illumination, should not have an intensity which exceeds about ten times that of the ambient light level, or about 1,500 footcandles. Preferably, the ratio between the ambient lighting in the dental operatory and the directable source of illumination is about three to one, and the corresponding ratio between the operatory ambient light and spot illumination in the oral cavity is about two to one, i.e. about 150 footcandles ambient lighting, 450 footcandles directable operatory lighting, and 900 footcandles for intracavity spot illumination. The levels of illumination may, of course, vary from these depending upon the particular preferences of the health professional. For the best long-term eye health of the professional, of course, it is highly desirable to minimize light intensity without compromising observability.

In addition to quality and quantity of light, contrast is important in the oral cavity. For example, the typical directable dental operatory light provides illumination in the oral cavity in a color correlated temperature range of between about 2,900 and 3,800 degrees Kelvin which is the color temperature of the tungsten halogen lamp source. Approximately 90% of all such sources of illumination installed in the U. S. provide a yellowish illumination characteristic of such a source. Spot illumination from the dental handpiece of the same correlated color temperature tends to blend with the overall oral cavity illumination, and this is undesirable. When, however, the correlated color temperature of the spot source is about 5,500 degrees Kelvin, good contrast is provided.

SUMMARY AND OBJECTS OF THE INVENTION

With the foregoing in mind, a primary object of the present invention is to provide an improved miniature hand-held spot source of illumination.

Another object of the present invention is to provide a novel miniature hand-held spot source of illumination which is particularly suited for use by health professionals to observe anatomical structures.

A further object of the present invention is to provide a novel method and apparatus for ameliorating long term eye damage to dental health professionals.

As yet another object, the present invention provides an efficient method and apparatus for spot illuminating anatomical structures in a manner which minimizes light intensity without adversely affecting observability.

A still further object of the present invention is to provide a dental handpiece having a color corrected light source operable to enhance the illumination of surfaces in the oral cavity.

More specifically, the present invention provides a miniature hand-held spot source of illumination and method particularly suited for use by health professionals to observe anatomical features. The invention comprises an elongate handle within which is mounted a source of illumination that is transmitted via an optical path to one or more light beams projecting from a proximal end of the handle. Desirably, the light beams are cast onto a drill or burr rotatably mounted at the proximal end of the handle. An optical filter preferably of the interference type is interposed in the light path in the handle for causing the correlated color temperature of the light beams to be about 2,000 degrees Kelvin different from the color temperature of the light source. Preferably, the correlated color temperature of the light beams are in a range of about 4,000 to about 7,000 degrees Kelvin when the light source in the handle is a tungsten-halogen lamp having a color temperature in a range of about 2,400 to about 3,400 degrees Kelvin. The light beams should have a color rendering index of at least about 70, and preferably greater than about 90. A selector may be provided in the handle for changing the correlated color temperature of the light beam as desired. Preferred parameters for spot and ambient lighting of a dental operatory are disclosed. Also, a method and apparatus for adjusting automatically the correlated color temperature of the light beams is provided.

BRIEF DESCRIPTION OF THE DRAWINGS

The foregoing and other objects, features and advantages of the present invention should become apparent from the following description when taken in conjunction with the accompanying drawings, in which:

FIG. 2 is an enlarged side elevational view of the hand-piece illustrated in FIG. 1, but with portions broken away and sectioned to illustrate certain details of construction;

FIG. 3 is a greatly enlarged fragmentary sectional view of a portion of the dental handpiece illustrated in FIG. 2;

FIG. 9 is a correlated color temperature (CCT) diagram for use in determining color temperature of any light source, including a tungsten halogen light-source; and FIG. 10 is a chromaticity diagram (CRI) corresponding to the CCT diagram of FIG. 9.

DESCRIPTION OF THE PREFERRED METHOD AND APPARATUS

Figure 1:
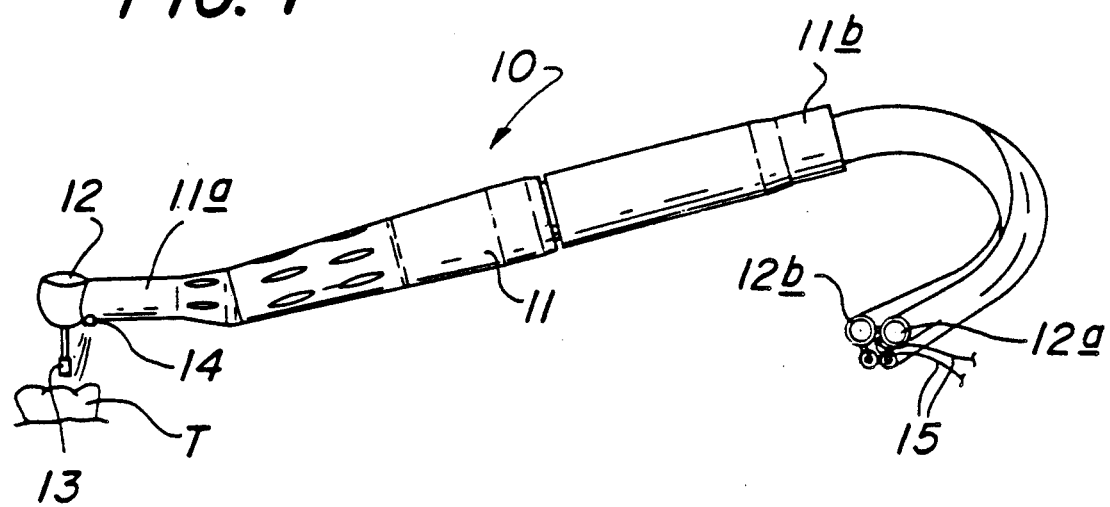
FIG. 1 is a side elevational view of a miniature hand-held spot source of illumination embodying the present invention.

Referring now to the drawings, FIG. 1 illustrates a hand-held instrument 10 for use in providing spot illumination of a work location. In the present instance, the instrument 10 is a dental handpiece which includes an elongated handle portion 11 having a proximal end portion 11a mounting an air turbine 12 for rotating either a drill or burr 13 adapted to operate on a tooth T in the conventional manner. The air supply and exhaust for the turbine 12 is provided by flexible elongated tubes 12a and 12b connected to the distal end 11b of the handle 11 and routed internally through the handle 11 in a conventional manner.

For purposes of illuminating the drill 13 and tooth T, it is known to provide the handpiece 10 with means for projecting a light beam in the region of the drill 13. To this end, the light beam projecting means includes at least one, and preferably a pair of light emission ports 14 mounted in the proximal end portion 11a of the handle 11 and canted in the direction of the drill 13 so as to project light laterally in the manner illustrated in FIG. 1. In the embodiment of FIG. 1, the light is provided by an electrically-powered lamp carried in the handle 11 and supplied with electricity by a power cable 15 associated with the air supply and exhaust tubes 12 and 12b.

As best seen in FIG. 2, the electrically-powered source of illumination includes a tungsten-halogen lamp 16 mounted adjacent to the distal end portion 11b of the handle 11 and disposed with its lamp light output lens 16a facing toward the proximal end 11a of the handle 11. See FIG. 3. Light from the lamp 16 is transmitted lengthwise of the handle 11 via an optical path provided by a series of endwise disposed optically-transparent elements, including a clad rod coupling 17, an optical transmission element 18, a fused fiber optic rod 19, and bifracted optical bundles 20 terminating in the light ports 14 at the proximal end portion 11a of the handpiece 10. Thus, light generated by the lamp 16 is transmitted lengthwise of the handle 11 and projected in optical beams B onto the drill 13.

As described thus far, the construction of the dental handpiece 10 is conventional. Such construction may be found in a handpiece sold by the assignee of the present application under the Trademark STAR Model 430 SWL.

Conventionally, the tungsten filament lamp has a maximum practical operating temperature of 3,200 degrees Kelvin. This is because operation at higher temperatures reduces the lamp life to unacceptable time frames from minutes to only a few hours of operation. At 3,200 degrees Kelvin, however, the quality of the light emitted from the optical projector ports 14 has a yellowish-red hue. While lamp life can be increased by reducing its operating temperature, operating at lower color temperatures simply exacerbates the light quality problem by shifting the hue further into the yellow range. Operation at significantly higher temperatures, not only shortens the lamp life, but also increases the intensity of the light emitted from the optical projector ports 14, and this is undesirable from the standpoint of the long term health of the eyes of the professionals using light emitted from the instrument.

According to the present invention, a means is provided in the optical path in the handle of the dental handpiece 10 for causing the color of the light emitted from the optical projector ports 14 to have a predetermined quality. To this end, a color correcting light filter 18a, preferably of the interference type, is provided on the optical transmission element 18 at the end thereof remote from the lamp 16. The optical filter 18a, as shown, is of the so-called interference type filter, and it is provided by serial electro-deposition of layers on the optical element 18 which, in the illustrated embodiment, is a cylinder of glass composition. Specifically, the filter 18a is characterized by the color correction filter transmission curve shown in FIG. 7. The evaporation film material includes titanium oxide and quartz. The coating should also meet the durability tests for adhesion, humidity and abrasion spelled out in MIL-C-48497, paragraphs 4.5.3.1,.2 and .3, respectively.

The element 18 may, however, be of a colored glass composition or may include a combination of colored glass and interference layers. Thus, the filter 18a is located in the optical path between the tungsten-halogen lamp 16 an the light projecting beams 14 at the proximal end portion of the instrument 11.

In the embodiment of FIGS. 2 and 3, the filter 18a is designed to filter the light from the lamp 16 so that the light beams B emitted from the optical port projectors 14 differ in correlated color temperature by about 2,000 degrees Kelvin relative to the light emitted by the lamp 16. In dental operatories where the ambient lighting and dental cavity source of illumination provides light of a yellowish hue, the filter 18a is designed to cause the light beams B to have a correlated color temperature in a range of about 4,000 to about 7,000 degrees Kelvin. More preferably, when the lamp 16 is of the tungsten-halogen type operated in a temperature range of between about 2,400 to about 3,400 degrees Kelvin, the filter 18a is designed so that the light beams produce a correlated color temperature of about 5,500 degrees Kelvin. Furthermore, the filter should also result in light beams B with a color rendering index of at least about 70, and more preferably greater than about 90. The intensity of illumination at the drill location, i.e. about 0.5 inches from the optical port projectors 14, should produce at least 150 footcandles. This results in a desirable spot source of illumination at that location of about 0.25 inches in diameter with good contrast relative to the surrounding tooth structure particularly when the light supplied to the oral cavity by the directable source has a yellowish hue, as in approximately 90 percent of the dental operatories in the U.S.

In the embodiments of FIGS. 2 and 3, a single optical filter element 18 is provided to produce light of the desired quality. While the filter element 18 can be removed from the dental handpiece and replaced should it be desired to change the color of the light beam emitted from the optical port projectors 14, removal and replacement would be time consuming, and hence, undesirable. Moreover, it would be necessary to keep a separate supply of filters at a different storage location, and this has the disadvantage of their either becoming damaged or lost, not to mention the inconvenience.

Figure 4:
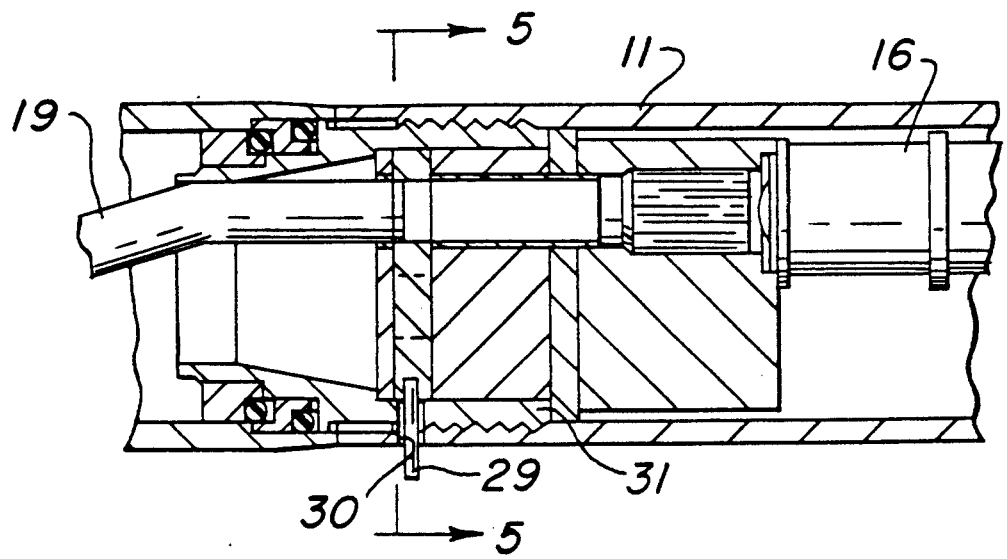
FIG. 4 is an enlarged fragmentary longitudinal cross-sectional view of a modified embodiment of the present invention.
Figure 5:
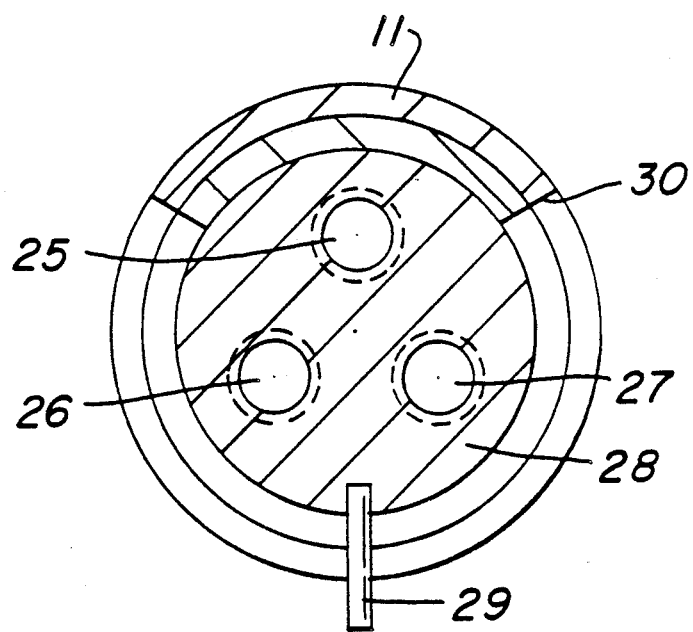
FIG. 5 is a transverse sectional view taken on line 5—5 FIG. 4
Figure 6:
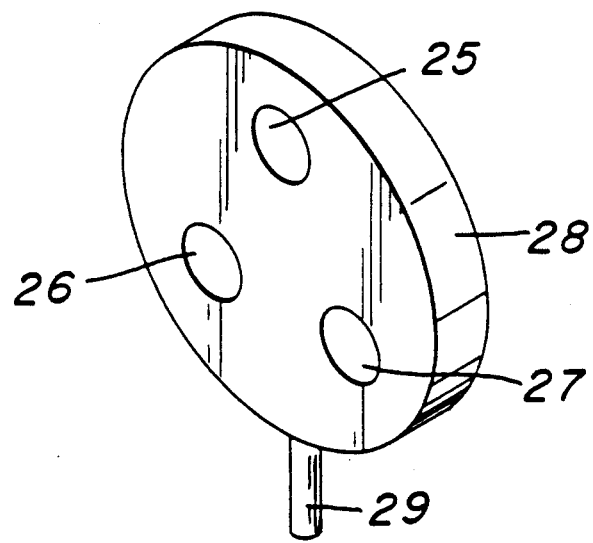
FIG. 6 is a perspective view of a component of the modified embodiment illustrated in FIG. 4.

In accordance with another embodiment of the present invention, a means is provided in the handle of the dental handpiece to enable filters of various construction to be selectively positioned in the optical path. To this end, the embodiment of FIGS. 4–6 is provided. In this embodiment, a plurality of filter elements, such as the elements 25, 26 and 27 are mounted at circumferentially spaced locations in circular disk 28 having a selector handle 29 projecting radially downward therefrom. As best seen in FIG. 4, the disk 28 is rotatably mounted for rotation about an axis extending lengthwise of the handle 11 in a cylindrical sleeve 31 threaded into the dental handpiece handle 11. The filter elements 25-27 are disposed radially relative to the rotational axis of the disk 28 so as to be capable of selectively being rotated into position in the light path between the lamp 16 and the fused fiber optic rod 19. Thus, the filter element 25 may be like in construction to the filter element 18 in the aforementioned embodiment. The filter element 26 may be constructed to provide light of a different correlated color temperature than the filter 25. The filter element 27, on the other hand, may simply include a clear glass element for those instances where a yellowish hue light might be desirable, such as when drilling in combination with application of a water mist. Thus, it should be apparent that the embodiment of FIGS. 4-6 enables the quality of the light emitted from the projectors 14 to be adjusted to suit the particular requirements of the professional.

In the embodiments of FIGS. 1-6, the source of illumination is provided in the handle of the handpiece, and electrical power is supplied to the source via electrical wires 15. In such embodiment, the intensity of the source of illumination is constant. If desired, however, suitable means may be provided for regulating the power supply to the lamp 16 for controlling the intensity of its output. Customarily, this is accomplished by providing a rheostat manually operable to adjust the power supply to the lamp 16.

In another embodiment of the present invention, the source of illumination for the dental handpiece can be placed at a remote location. To this end, as best seen in the schematic diagram of FIG. 8, (sheet 1) a dental handpiece 32 is provided with light from a source such as a tungsten-halogen lamp 35 with an elliptical reflector via an elongate optical fiber cable 33 and transition piece 34. An advantage of this construction is that it enables a variety of different types of lamps of various operating temperatures and spectrums to be used to provide the light for the beams B. For instance, such sources of illumination may include metal halide gas filled arc lamps, including mercury, sodium or xenon (confined or unconfined) or combination gas filled arc lamps. In this embodiment either plural lamps or plural filters can be movably mounted into and out of registry with the transition piece 34, much like the filters are moved in the embodiment of FIGS. 4-6. In this embodiment, however, the lamps may be made larger in order to overcome the additional length required for this type of light delivery system.

Figure 8:
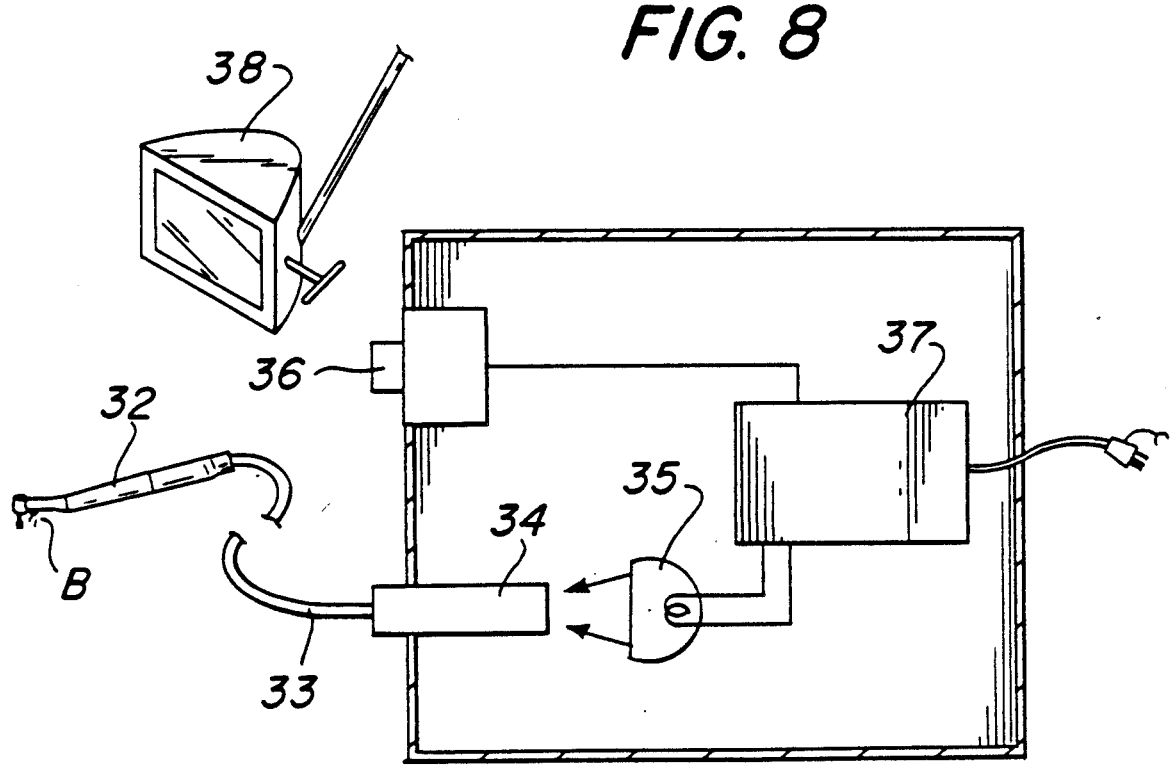
FIG. 8 is a schematic illustration of a further modified embodiment of the present invention.

The embodiment of FIG. 8 may be modified to provide automatic adjustment of light intensity, depending upon conditions within the dental operatory. To this end, a means is provided for sensing the level of illumination produced by the directable illumination source 38 in the dental operatory and for automatically regulating power to the remote lamp 35. As best seen in the FIG. 8 schematic, this may be accomplished by means of a photosensitive cell 36 located so as to sense the light emitted from the directable source 35 and an appropriate amplifier and control unit 37 which interconnects the cell 36 and lamp 35 and is powered by a conventional 120 VAC source. With this system, the level of illumination sensed by the cell 36 can be fed into the amplifier and control unit 37 which then can control the power to the lamp 35 in accordance with conventional electronic circuitry. This permits the level of illumination of the light from the handpiece 32 to be adjusted automatically in response to illumination produced by the directable source 38, thereby insuring a desirable amount of light intensity contrast between the spot source and the generalized source in the oral cavity, such as at the relative levels noted heretofore.

Figure 7:
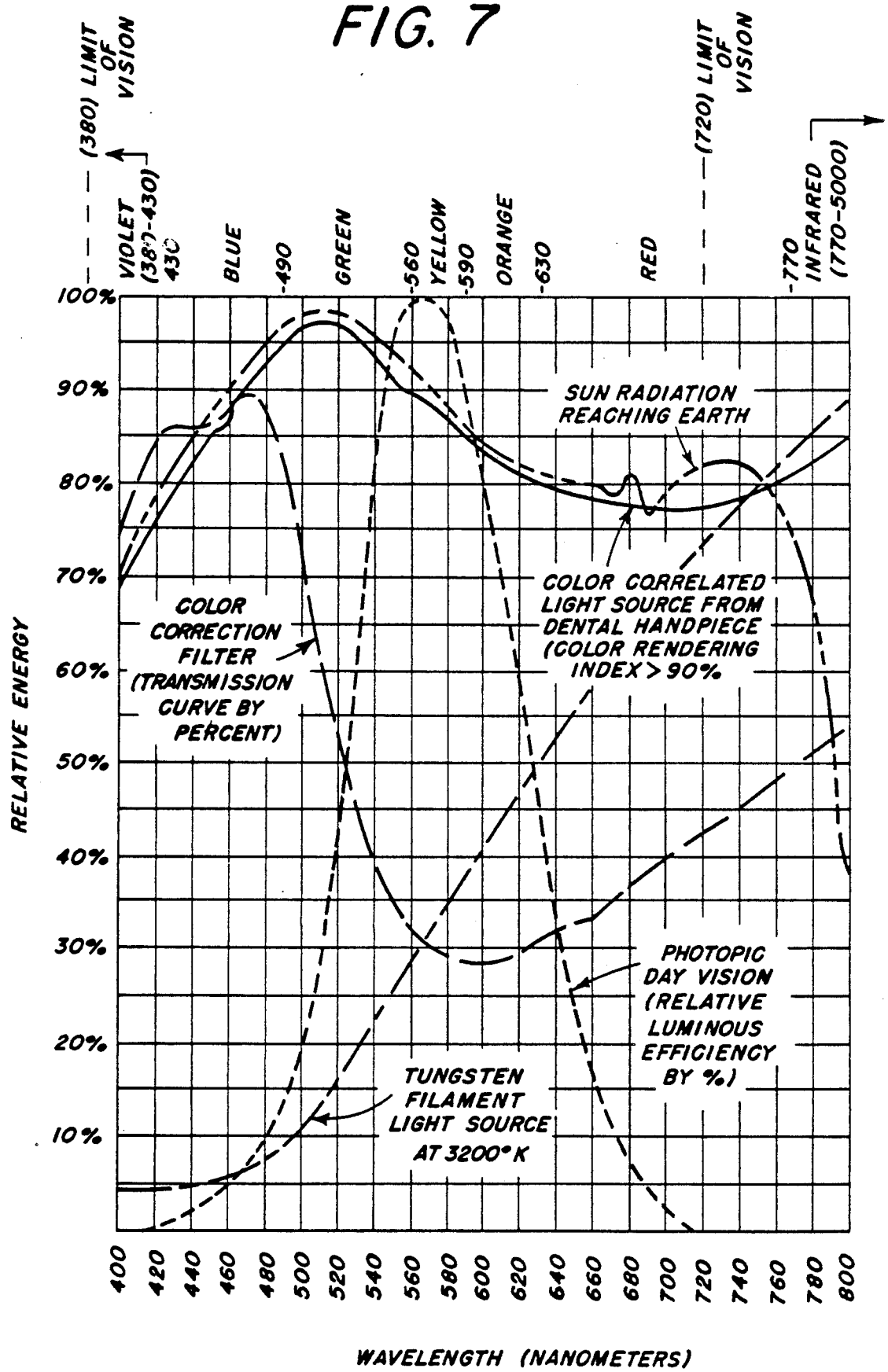
FIG. 7 is a graph illustrating certain physical relations involved in the present invention.

The theoretical underpinnings of the present invention may best be understood by reference to the diagrams illustrated in FIG. 7, 9 and 10. FIG. 7 is a plot of relative visible light energy with respect to wavelength. The triple-dashed curve spanning the visible spectrum is denominated Sun Radiation Reaching Earth. Note that it peaks between at a wavelength of about 500 to 520 nanometers, and falls off rapidly above about 760 nanometers. The dashed curve denominated Photopic Day Vision (relative luminous efficiency by percent) is a typical bell-shaped curve which peaks slightly above 560 nanometers. The single-line curve denominated tungsten filament light source at 3,200 degrees Kelvin rises from a low relative energy level at shorter wavelengths, such as 400 nanometers, and increases to a relative energy level in excess of 80 percent at about 800 nanometers. The broken line curve denominated Color Correction Filter (transmission curve by percent) represents the relative energy passed by the filter at various wavelengths. In the present invention, the net effect of the color correction filter on the light generated by the tungsten filament light source is the solid line curve denominated Color Correlated Light Source From Dental Handpiece (color rendering index greater than 90 percent) which generally parallels in close proximity the Sun Radiation Curve over the visible spectrum of light.

FIGS. 9 and 10, when viewed together, indicate the shift in correlated color temperature that results when a tungsten halogen lamp is operated at different temperatures. For instance, operation at temperatures lower than 3,200 degrees Kelvin shifts the hue to the red and infrared portion of the spectrum. Operation at temperatures higher than 5,500 degrees Kelvin produces white light and a color rendering index greater than 90. Operation at about 4,000 degrees Kelvin shifts the hue so that the light has a color rendering index of greater than about 70.

The referenced curves are applicable to tungsten filament lamps. If arc type lamps were used in place of tungsten filament lamps, such as described heretofore with respect to the embodiment of FIG. 8, it might be necessary to reduce the color correlated temperature of the light beams B, rather than increasing it, because such lamps have substantially different light output spectrums requiring different color correction filter transmission curves.

In view of the foregoing, it should be apparent that the present invention provides a miniature spot source of illumination particularly suited for use in combination with a dental handpiece to improve the visual efficiency of the health professional. By causing the color of the spot source to have a correlated color temperature of about 5,500 degrees Kelvin with a color rendering index of greater than 90 and type of white light source is provided to maximize the simulation of all specialized color sensitive cones in the eye, particularly those cones in the eye detail focusing area in the fovea of the retina. This enables the intensity of the light required to observe details to be reduced, because there is a greater stimulation of the total specialized cone population in the eye. Reduction in light intensity is desirable to minimize possible eye damage that might occur when the eye is subjected to intense illumination for prolonged periods of time. As a result, the present invention functions to minimize declines in long-term visual efficiency and overall eye health. This is accomplished, moreover, without adversely affecting the perception by the health professional of a decrease in the level of illumination. Furthermore, by supplying a complete visible spectrum in a spot source in the oral cavity, the concentration or strength of the reflected color is improved.

Thus, while a preferred method and apparatus has been described in detail, various modifications, alterations and changes may be made without departing from the spirit and scope of the present invention as defined in the appended claims.

We claim:

1. A hand-held instrument for use in combination with an overall source of illumination for providing an auxiliary spot source of illumination of a work location in a body cavity comprising:
   handle means having a proximal end portion adapted to be positioned adjacent to said work location;
   light projection means located on said handle means adjacent to said proximal end portion for projecting at least one beam of light toward said work location;
   means carried by said handle means for providing therein a source of the light emitted from said light projection means; and
   filter means carried by said handle means in an optical path between said light source and said projection means for causing the light beam to have a correlated color temperature in a range of about 4000 to about 7000 degrees Kelvin;
   said spot source of illumination providing a discrete region of illumination which is smaller than the region of illumination provided by said overall source of illumination and which is also of a proper color rendering index to cause maximum stimulation of the fovea of the eye of the user when viewing the body cavity under both sources of illumination.

2. An instrument according to claim 1 wherein said filter means causes said light emitted from said projector means to have a color rendering index of at least about 70.

3. An instrument according to claim 2 wherein said light source is provided by a tungsten filament lamp normally operable in a range of about 2400 to about 3400 degrees Kelvin.

4. An instrument according to claim 1, wherein said filter means includes an optical element having either an optical coating or color composition or combination of a coating and color composition mounted in said handle means and disposed in a light path between said light source and said projection means.

5. An instrument according to claim 4, wherein said light source includes an electrically powered lamp mounted in said handle means remote from said proximal end portion thereof.

6. An instrument according to claim 5, wherein said lamp has a tungsten filament normally operable at a temperature in a range of about 2400 to about 3400 degrees Kelvin.

7. An instrument according to claim 1 including selector means carried by said handle means and operable externally thereof for moving said filter means relative to said light source means for changing the correlated color temperature of the light emitted by said projector means.

8. An instrument according to claim 7 wherein said light source is stationary in said handle and said selector means includes a plurality of filter elements selectively displaceable into and out of said light path.

9. An instrument according to claim 8 wherein said selector means includes a barrel rotatable about an axis extending lengthwise of said handle means and mounting said filter elements at circumferentially spaced locations.

10. An instrument according to claim 1 wherein said light source is located separate from said handle means and light from said source is transmitted into said handle means via at least one optical fiber.

11. An instrument according to claim 1 wherein the color temperature of the light source is adjustable, and including means for sensing the correlated color temperature of ambient light in the vicinity of the work surface and means operable automatically to adjust the operating light intensity of the light source to maintain a light intensity difference between the light emitted from the projector means and the light source.

12. An instrument according to claim 1 including a tool mounted on said proximal end portion of said handle means for operating in an oral cavity, and wherein said projector means casts said light beam onto said tool.

13. A hand-held instrument particularly suited for use by a health professional to view and operate upon anatomical portions of a patient illuminated by an overall source of illumination, comprising:
   an elongate handle having a proximal end portion adapted to be positioned adjacent to the anatomical portion to be viewed and operated upon;
   a tool carried on said proximal end portion of said handle for operating of said patient;
   light projection means located on said handle adjacent its proximal end portion for directing at least one beam of visible light laterally thereof toward said tool for providing a spot of illumination;
   an electrically-powered source of light mounted in said handle remote from said light projection means for generating a source of light of a predetermined correlated color temperature;
   means providing an optical path between said light source in said handle and said light beam projection means; and
   at least one optical filter mounted in said handle across said light path between said light source and said light projection means for causing said light beam to have a preselected correlated color temperature in a range of about 4000 to about 7000 degrees Kelvin;
   said spot of illumination adjacent to said tool providing a distinct region of illumination which is smaller than said overall source of illumination and which, when reflected from a surface undergoing observation, is also of a proper color rendering index to cause maximum stimulation of the fovea of the eye of the health professional when using the tool to operate upon the patient.

14. An hand-held instrument according to claim 13, including selector means operable externally of said handle for moving said filter selectively into and out of said optical path.

15. A hand-held instrument according to claim 13, including means mounting a plurality of optical filters in said handle, and selector means operable externally of said handle for positioning a selected one of said filters in said optical path in response to movement of said selector means.

16. A hand-held instrument according to claim 13 wherein said source of light in said handle is provided by a tungsten filament lamp operable in a temperature range of about 2400 to about 3400 degrees Kelvin.

17. A hand-held instrument according to claim 13 wherein said optical filter in said handle causes said light beam to have a color rendering index of at least 90.

18. A hand-held instrument according to claim 13 wherein said light source has a correlated color temperature of about 3200 degrees Kelvin, said filter provides said light beam with a correlated color temperature of about 5500 degrees Kelvin and a color rendering index of at least about 90.

19. In an operatory having a directable source of generalized artificial illumination providing visible ambient light of a predetermined color temperature greater than about 3000 degrees Kelvin and a hand-held instrument having a tool and a spot source of artificial illumination for enabling a health professional to view and operate upon a discrete portion of a patient's anatomy, a method of providing said spot illumination while minimizing long term eye damage to the health professional, comprising the steps of:
  providing in said hand-held spot source visible light of a predetermined correlated color temperature;
  forming said visible light into at least one beam projectable from said hand-held stop source into the vicinity of said discrete portion of anatomy; and
  filtering said visible light before being projected from said hand-held spot source to cause said beam to have a correlated color temperature in a range of about 4000 to about 7000 degrees Kelvin and to provide a discrete smaller region of light which when reflected from a surface undergoing observation in the operatory, is also of a proper color rendering index to cause maximum stimulation of the fovea of the eye of the user of the instrument at least while operating on said portion of anatomy with said tool.

20. A method according to claim 19 wherein said visible light in said providing step has a correlated color temperature in a range of about 2400 to about 3400 degrees Kelvin and said filtering step causes said light beam to have a correlated color temperature in a range of about 4000 to about 7000 degrees Kelvin.

21. A method according to claim 19 wherein said light beam has a color rendering index of at least about 70.

22. A method according to claim 19 wherein said directable source of generalized artificial illumination provides a predetermined level of light on the patient's oral cavity and anatomy, and said light beam provided by said hand-held source has a level of light intensity in lumens which is about one to three times the level of light intensity of said directable generalized source.

23. A method according to claim 19 including the steps of sensing the level of illumination in said operatory and automatically controlling the correlated color temperature of said light beam in response to the sensed level of illumination.

* * * * *